(12) United States Patent
Ono et al.

(10) Patent No.: US 9,421,395 B2
(45) Date of Patent: Aug. 23, 2016

(54) ULTRAVIOLET LIGHT IRRADIATION DEVICE FOR SUNTAN

(71) Applicant: NICHIA CORPORATION, Anan-shi, Tokushima (JP)

(72) Inventors: Jiro Ono, Tokyo (JP); Hideji Tanizaki, Amstelveen (NL); Yuji Itsuki, Anan (JP)

(73) Assignee: NICHIA CORPORATION, Anan-Shi (JP)

( * ) Notice: Subject to any disclaimer, the term of this patent is extended or adjusted under 35 U.S.C. 154(b) by 0 days.

(21) Appl. No.: 14/856,668

(22) Filed: Sep. 17, 2015

(65) Prior Publication Data

US 2016/0082280 A1 Mar. 24, 2016

(30) Foreign Application Priority Data

Sep. 19, 2014 (JP) .................................. 2014-191476

(51) Int. Cl.
*A61N 5/06* (2006.01)

(52) U.S. Cl.
CPC ....... *A61N 5/0614* (2013.01); *A61N 2005/0629* (2013.01); *A61N 2005/0652* (2013.01); *A61N 2005/0661* (2013.01)

(58) Field of Classification Search
USPC ........ 250/453.11, 492.1, 492.2, 493.1, 503.1, 250/504 R
See application file for complete search history.

(56) References Cited

U.S. PATENT DOCUMENTS

2009/0216302 A1    8/2009   Smolka

FOREIGN PATENT DOCUMENTS

| JP | 2006-318847 A | 11/2006 |
| JP | 2006-525838 A | 11/2006 |
| JP | 2007-504925 A | 3/2007 |
| JP | 2010-505566 A | 2/2010 |
| JP | 2015-011852 A | 1/2015 |
| WO | WO 2004/098708 A1 | 11/2004 |
| WO | WO 2004/098709 A1 | 11/2004 |
| WO | WO 2005/000389 A2 | 1/2005 |
| WO | WO 2008/043520 A2 | 4/2008 |

*Primary Examiner* — Nicole Ippolito
*Assistant Examiner* — Hanway Chang
(74) *Attorney, Agent, or Firm* — Squire Patton Boggs (US) LLP

(57) ABSTRACT

The UV light irradiation device includes a chamber having a space for accommodating therein an irradiation target, and a plurality of light-emitting diodes provided at an inner surface of the chamber. A controller is configured to control lighting of the plurality of light-emitting diodes. The light-emitting diodes include a plurality of first light-emitting diodes, each having a peak wavelength in a range of 280 nm to 310 nm, and a plurality of second light-emitting diodes, each having a peak wavelength in a range of 310 nm to 405 nm. The controller includes a lighting control section that is configured to light up the first light-emitting diode before lighting up the second light-emitting diode.

20 Claims, 3 Drawing Sheets

ULTRAVIOLET LIGHT IRRADIATION DEVICE FOR SUNTAN

CROSS-REFERENCE TO RELATED APPLICATIONS

This application claims priority on Japanese Patent Application No. 2014-191476 filed on Sep. 19, 2014, the disclosure of which is incorporated by reference herein.

BACKGROUND OF THE INVENTION

1. Field

The present disclosure relates to an ultraviolet (UV) light irradiation device for suntan and, more particularly, to a UV light irradiation device for suntan using a light-emitting diode.

2. Description of the Related Art

A UV light irradiation device for suntan is a machine designed to tan and darken human skin by artificially irradiating the skin with ultraviolet (UV) rays.

Conventionally, UV light irradiation devices using fluorescent lamps have been widely used as the UV light irradiation device for suntan. In recent years, one type of UV light irradiation device for suntan has been proposed that employs a light-emitting diode, as disclosed in JP 2007-504925.

The use of the light-emitting diode as a UV light source enables selective irradiation with the UV light having a specific peak wavelength, compared to the use of the fluorescent lamp as the UV light source.

It is generally known that when an irradiation target, for example, skin is irradiated with UV light, the skin would be damaged. In the use of UV light irradiation devices for suntan, it is desirable to reduce the amount of irradiation from the UV light as little as possible. However, the conventional UV light irradiation devices for suntan using the fluorescent lamps, and the UV light irradiation devices using the light-emitting diodes as mentioned in JP 2007-504925 have difficulty in obtaining the adequate tanning effect while suppressing damage to the skin as the irradiation target due to irradiation with the UV light.

SUMMARY

Accordingly, it is an object of the present disclosure to provide a UV light irradiation device for suntan that can efficiently attain the desired tanning effect while suppressing the damage to skin as the irradiation target as little as possible.

To achieve the above-mentioned object, a UV light irradiation device according to an embodiment of the present invention includes a chamber having a space for accommodating therein an irradiation target. A plurality of light-emitting diodes provided at an inner surface of the chamber, and a controller is configured to control lighting of the plurality of light-emitting diodes. The plurality of light-emitting diodes includes a plurality of first light-emitting diodes, each having a peak wavelength in a range of 280 nm to 310 nm. A plurality of second light-emitting diodes are provided, each having a peak wavelength in a range of 310 nm to 405 nm. The controller includes a lighting control section that is configured to light up the first light-emitting diode before lighting up the second light-emitting diode.

In the UV light irradiation device according to embodiments of the present invention, the first light-emitting diode is lit up before lighting up the second light-emitting diode, which can more efficiently attain the tanning effect, while suppressing the damage to, for example, the skin of the irradiation target.

DETAILED DESCRIPTION

Preferred embodiments of the present invention, which are illustrated in the accompanying drawings, will be described in detail. Note that a UV light irradiation device for suntan to be mentioned later is intended to embody the technical idea of the present invention, and not to restrict the scope of the present invention to the following embodiments, unless otherwise specified. The contents mentioned in one embodiment can also be applied to other embodiments. In some drawings, the sizes or positional relationships of elements, etc., are emphasized to clarify the description below.

Figure 1:
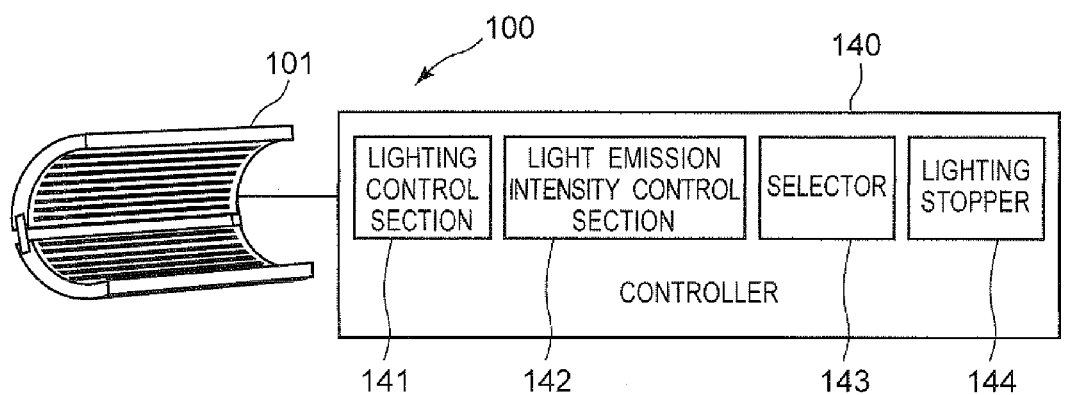
FIG. 1 is a schematic diagram showing the entire configuration of a UV light irradiation device for suntan according to a first embodiment of the present invention.
Figure 2:
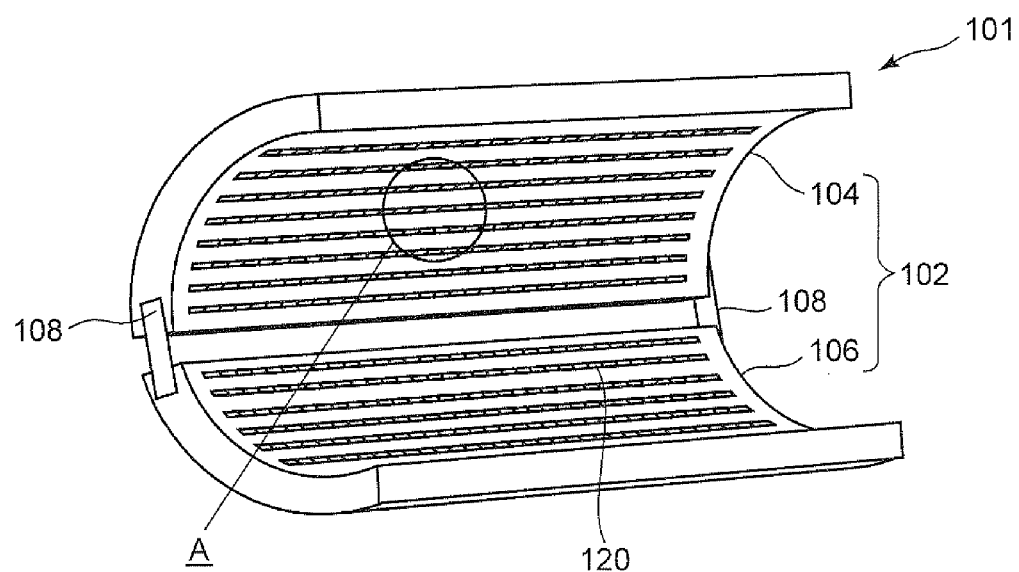
FIG. 2 is a perspective view of a UV light irradiation portion in the UV light irradiation device for suntan in the first embodiment of the present invention.
Figure 3:
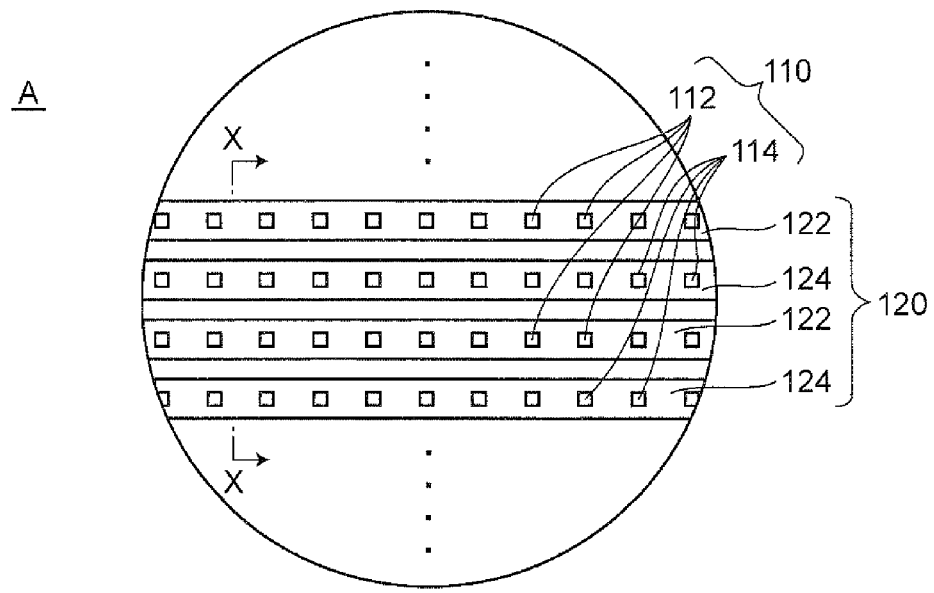
FIG. 3 is an enlarged view of a part A shown in FIG. 2, specifically, a schematic plan view showing first longitudinal substrates and second longitudinal substrates that are provided in the UV light irradiation portion of the UV light irradiation device for suntan in the first embodiment of the present invention.

FIG. 1 is a schematic diagram showing the entire configuration of a UV light irradiation device for suntan according to a first embodiment. A UV light irradiation device 100 for suntan in the first embodiment includes a UV light irradiation portion 101 and a controller 140. FIG. 2 is a perspective view of the UV light irradiation portion 101 in the UV light irradiation device 100 for suntan in the first embodiment. FIG. 3 is an enlarged view of a part A shown in FIG. 2, specifically, a schematic plan view showing first longitudinal substrates 122 and second longitudinal substrates 124 that are provided in the UV light irradiation portion 101 in the first embodiment. The UV light irradiation device 100 for suntan is a UV light irradiation device for suntan using a light-emitting diode as a UV light source. The UV light irradiation portion 101 includes a chamber 102 and a plurality of light-emitting diodes 110 provided at the inner surface of the chamber 102.

Here, particularly, in the UV light irradiation device 100 for suntan in the first embodiment, the plurality of light-emitting diodes 110 includes a plurality of first light-emitting diodes 112, each having a peak wavelength in a range of 280 nm to 310 nm, and a plurality of second light-emitting diodes 114, each having a peak wavelength in a range of 310 nm to 405 nm. The controller 140 includes a lighting control section 141 that lights up the first light-emitting diodes 112 before lighting up the second light-emitting diodes 114.

That is, focusing on the fact that when humans are bathed in the sunlight to have their skin tanned, first, the skin is turned red and after a while turned brown, the present inventors have considered that it would be possible to suntan the skin with a smaller amount of irradiation of ultraviolet rays by producing a melanin pigment of a red pigment in the skin and then darkening this melanin pigment. Based on the consideration, the present inventors have achieved the present invention.

Specifically, when no or a little melanin pigment is produced, the UV light irradiation device 100 for suntan in the first embodiment irradiates the skin with light from the first light-emitting diode 112 for generating any melanin pigment, while suppressing the amount of irradiation of light from the second light-emitting diode 114 having a peak wavelength in a range of 310 nm to 405 nm for darkening the melanin pigment. After a certain amount or more of melanin pigment is produced, the UV light irradiation device 100 irradiates the skin with the light from the second light-emitting diode 114 having the peak wavelength in the range of 310 nm to 405 nm for darkening the melanin pigment, while suppressing irradiation of the light from the first light-emitting diode 112 for producing the melanin pigment.

The UV light irradiation device 100 for suntan in the first embodiment will be described in detail.

Figure 4:
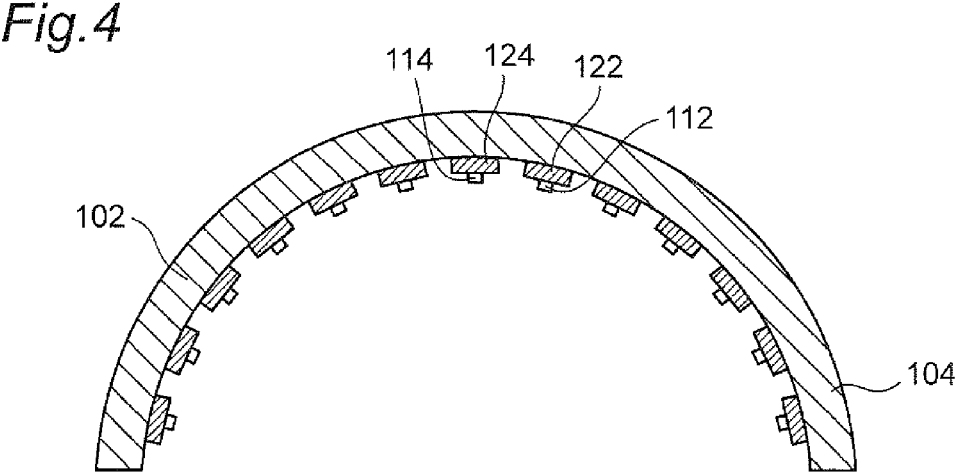
FIG. 4 is a cross-sectional view taken along the line X-X of FIG. 3.

As shown in FIG. 2, the chamber 102 may include a first cover 104 and a second cover 106, which have respective outer surfaces and inner surfaces, and a coupling element 108. The first cover 104 and the second cover 106 are coupled to each other openably and closably by the coupling element 108. The first cover 104 and the second cover 106 are superimposed with their inner surfaces facing each other, whereby the two inner surfaces form a substantially columnar cavity, in which the irradiation target (for example, human) can be accommodated. FIG. 4 is a cross-sectional view taken along the line X-X of FIG. 3, specifically, a cross-sectional view of the first cover 104 in the UV light irradiation portion 101. However, FIG. 4 shows the cross-section of not only the part A in FIG. 3 but the first cover 104 entirely. As shown in FIG. 4, the plurality of first light-emitting diodes 112 mounted on each of the plurality of first longitudinal substrates 122 and the plurality of the second light-emitting diodes 114 mounted on each of the plurality of second longitudinal substrates 124 may be provided at the inner surface of the first cover 104. Likewise, the plurality of first light-emitting diodes 112 mounted on each of the plurality of first longitudinal substrates 122 and the plurality of second light-emitting diodes 114 mounted on each of the plurality of second longitudinal substrates 124 may be provided at the inner surface of the second cover 106. The plurality of first light-emitting diodes 112 and the plurality of second light-emitting diodes 114 may be provided to apply the light to the irradiation target accommodated in the substantially columnar space, which is formed by the first cover 104 and the second cover 106. Note that the space of the chamber can be formed in a substantially polygonal prism shape by employing three or more covers.

The plurality of light-emitting diodes 110 includes the plurality of first light-emitting diodes 112 having a peak wavelength in a range of 280 nm to 310 nm, and the plurality of second light-emitting diodes 114 having a peak wavelength in a range of 310 nm to 405 nm. UV having a wavelength range of 280 nm to 310 nm is classified as an ultraviolet-B wave (UVB), and UV having a wavelength range of 310 nm to 405 nm is classified as an ultraviolet-A wave (UVA) herein. The plurality of first light-emitting diodes 112 having the peak wavelength in a range of 280 nm to 310 nm can irradiate the irradiation target with the UVB light to produce the melanin pigment in the skin of the irradiation target. On the other hand, the plurality of second light-emitting diodes 114 having the peak wavelength in a range of 310 nm to 405 nm can irradiate the irradiation target with the UVA light to darken the melanin pigment produced in the skin of the irradiation target.

As shown in FIG. 1, the controller 140 of the first embodiment includes the lighting control section 141 that turns on the first light-emitting diodes 112 before lighting up the second light-emitting diodes 114.

The mechanism that darkens the skin by irradiation with the UV light involves producing a melanin pigment by irradiation with the UVB light, and then darkening the melanin pigment by irradiation with the UVA light. The tanning level of the skin by irradiation with the UV light depends on the amount of melanin pigment produced by irradiation with the UVB light. Thus, the tanning effect can be controlled by controlling the amount of irradiation with the UVB light. In the first embodiment, the irradiation with the UVB light by means of the first light-emitting diodes 112 starts before the irradiation with the UVA light by the second light-emitting diodes 114 starts. With this arrangement, to obtain the tanning effect desired by the irradiation target, the minimum amount of UVB light required for the desired tanning effect is applied to produce the melanin pigment, and then the minimum amount of UVA light required in accordance with the amount of the produced melanin pigment has only to be applied, so that the adequate tanning effect can be obtained while suppressing the damage to the skin of the irradiation target.

Figure 5A:
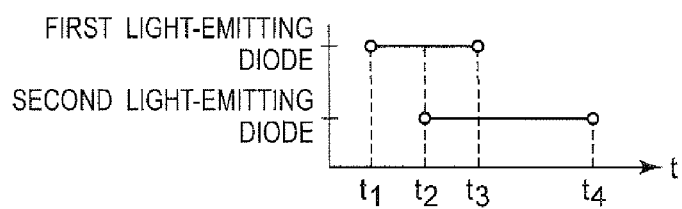
FIG. 5A is a timing chart showing one example of the operations of lighting devices of a first light-emitting diode and a second light-emitting diode.
Figure 5B:
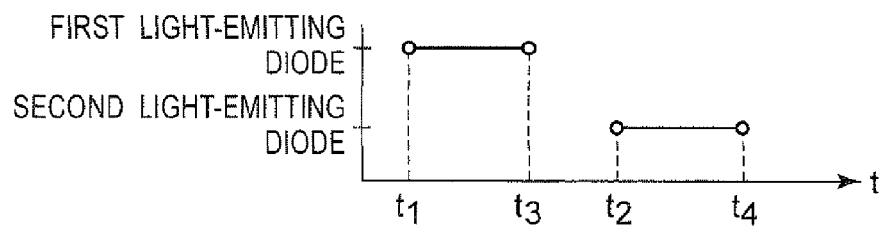
FIG. 5B is a timing chart showing another example of the operations of lighting devices of the first light-emitting diode and the second light-emitting diode.

In the first embodiment, the lighting control section 141 may light up the second light-emitting diodes 114 before stopping lighting the first light-emitting diodes 112. Alternatively, the lighting control section 141 may light up the second light-emitting diodes 114 after stopping lighting the first light-emitting diodes 112. FIGS. 5A and 5B are timing charts showing examples of the operations of lighting devices of the first light-emitting diodes and the second light-emitting diodes. For example, as illustrated in the timing charts of FIGS. 5A and 5B, the lighting control section 141 controls lighting of the first light-emitting diodes 112 and the second light-emitting diodes 114. In FIGS. 5A and 5B, the horizontal axis indicates the time (t), in which $t_1$ is a time when the first light-emitting diodes 112 start lighting; $t_3$ is a time when the first light-emitting diodes 112 stop lighting; $t_2$ is a time when the second light-emitting diodes 114 start lighting; and $t_4$ is a time when the second light-emitting diodes 114 stop lighting. As shown in FIG. 5A, after the lighting of the first light-emitting diodes 112 starts (at the time $t_1$), and before the lighting is stopped (at the time $t_2$), the lighting of the second light-emitting diodes 114 may start (at the time $t_2$). Alternatively, as shown in FIG. 5B, after some time has passed since the lighting of the first light-emitting diodes 112 starts (at the time $t_1$) and stops (at the time $t_3$), the lighting of the second light-emitting diodes 114 may start (at the time $t_2$).

In the first embodiment, the lighting control section 141 can also be configured to individually adjust the lighting time of each of the plurality of the first light-emitting diodes 112 and the lighting time of each of the plurality of the second light-emitting diodes 114. With this arrangement, the respective lighting times of the plurality of first light-emitting diodes 112 can be adjusted to control the amount of melanin produced in the skin of the irradiation target, and the respective lighting times of the plurality of second light-emitting diodes 114 can be adjusted to control the level of darkening of the skin of the irradiation target. Alternatively, based on information about the relationship between the amounts of irradiation of the UVA light and UVB light and the level of darkening of the skin of the irradiation target, the first light-emitting diodes 112 may be lit up only for the time required depending on the desired darkening level, and thereafter the second light-emitting diodes 114 may be lit up only for the time required depending on the desired darkening level. This can obtain the desired tanning effect without excessive irradiation with the UVA light and the UVB light (that is, while suppressing the damage to the skin due to the irradiation with the UV light). Thus, the UV light irradiation device for suntan can also achieve energy saving.

In the first embodiment, the first light-emitting diodes 112 and the second light-emitting diodes 114 may be alternately lit up. Specifically, for example, the first light-emitting diodes 112 may be lit up to irradiate the target with the UVB light, and then the lighting of the first light-emitting diodes 112 may be stopped. Thereafter, the second light-emitting diodes 114 may be lit up to irradiate the target with the UVA light, and then the first light-emitting diodes 112 may be lit up again, causing the irradiation with the UVB light. This cycle may be repeatedly executed. When the desired tanning level is reached, the lighting may be terminated. In this way, the melanin pigment is gradually produced by irradiation with the UVB light, and together with this, the skin can be darkened and settled little by little by irradiation with the UVA light. The repetition of this cycle allows the irradiation target to gradually approach the desired tanning level without excessive irradiation with the UVA light and the UVB light (that is, while suppressing the damage to the skin due to the irradiation with the UV light), and further can prevent the darkening level of the skin of the irradiation target from exceeding the desired level. The desired tanning level can be achieved even with no information on the relationship between the amounts of irradiation with the UVA light and the UVB light and the darkening level of the skin of the irradiation target.

As shown in FIG. 1, the controller 140 of the first embodiment may include a light emission intensity control section 142 that individually controls the light emission intensities of lights from the plurality of first light-emitting diodes 112 and the light emission intensities of lights from the plurality of second light-emitting diodes 114. The respective light emission intensities of lights from the plurality of first light-emitting diodes 112 can be adjusted to control the amount of melanin produced in the skin of the irradiation target. The respective light emission intensities of lights from the plurality of second light-emitting diodes 114 can be adjusted according to the amount of produced melanin, thereby preventing the skin of the irradiation target from being irradiated with the excessive UVA light. Therefore, the tanning effect can be obtained while suppressing the damage to the skin due to irradiation with the UV light.

As shown in FIG. 2, the UV light irradiation portion 101 of the first embodiment includes substrates 120 provided at the inner surface of the chamber. The plurality of light-emitting diodes 110 may be provided on each of the substrates 120. As shown in FIG. 3, the substrates 120 may include the plurality of first longitudinal substrates 122 with the plurality of first light-emitting diodes 112 respectively mounted thereon, and the plurality of second longitudinal substrates 124 with the plurality of second light-emitting diodes 114 respectively mounted thereon.

Each first longitudinal substrate 122 may be made of one piece extending in one line in the longitudinal axis direction of the chamber 102, or may be made of two or more pieces divided. Likewise, each second longitudinal substrate 124 may be made of one piece extending in one line in the longitudinal axis direction of the chamber 102, or may be made of two or more pieces divided.

As shown in FIG. 3, the first light-emitting diodes 112 may be mounted at predetermined intervals in the long-side direction of the first longitudinal substrate 122. Likewise, the second light-emitting diodes 114 may be mounted at predetermined intervals in the long-side direction of the second longitudinal substrate 124.

In the first embodiment, as shown in FIG. 3, the first and second longitudinal substrates 122 and 124 may be alternately arranged in the short axis direction of the chamber 102.

The first longitudinal substrates 122 may be arranged in the short-side direction of the first longitudinal substrate 122 such that the plurality of first light-emitting diodes 112 provided on the respective first longitudinal substrates can uniformly apply the UVB light to the irradiation target. For example, the two first longitudinal substrates 122 sandwiching the second longitudinal substrate 124 may be mounted at the same interval as that between the plurality of first light-emitting diodes 112 mounted in the long-side direction of the first longitudinal substrate 122. In this way, the irradiation target can be uniformly irradiated with the UVB light by means of the plurality of first longitudinal substrates.

Likewise, the plurality of second longitudinal substrates 124 may be arranged in the short-side direction of the second longitudinal substrate 124 such that the plurality of second light-emitting diodes 114 provided on the respective second longitudinal substrates can uniformly apply the UVA light to the irradiation target. For example, the two second longitudinal substrates 124 sandwiching the first longitudinal substrate 122 may be mounted at the same interval as that between the plurality of second light-emitting diodes 114 mounted in the long-side direction of the second longitudinal substrate 124. In this way, the irradiation target can be uniformly irradiated with the UVA light by means of the plurality of second longitudinal substrates 124.

The plurality of first longitudinal substrates 122 may be arranged such that a certain distance, or more, is kept between the irradiation target and the respective first light-emitting diodes 112. Likewise, the plurality of second longitudinal substrates 124 may be arranged such that a certain or more distance is kept between the irradiation target and the respective second light-emitting diodes 114. Taking into consideration the directivity of the light-emitting diode, the plurality of first longitudinal substrates 122 and the plurality of second longitudinal substrates 124 have such arrangements that the UV lights emitted from the light-emitting diodes can be uniformly applied to the irradiation target. This arrangement can exhibit the evenly good-looking tanning effect on the irradiation target, which can prevent the skin from being damaged due to the excessive irradiation with the UV light only on a specific part of the irradiation target.

Taking into consideration the fact that as the distance from the light-emitting diode is increased, the intensity of UV light emitted from the light-emitting diode is weakened, the first longitudinal substrates 122 may be disposed to keep the distance between the irradiation target and each of the plurality of first light-emitting diodes 112 within a certain range. Likewise, the second longitudinal substrates 124 may be arranged to keep the distance between the irradiation target and each of the plurality of second light-emitting diodes 114 within a certain range. Each of the first longitudinal substrates 122 and each of the second longitudinal substrates 124 may be preferably arranged to have substantially the same distance from the corresponding part of the irradiation target. To achieve that, for example, a flexible substrate is used for the plurality of first longitudinal substrates 122 and the plurality of second longitudinal substrates 124, so that these substrates 122 and 124 can be disposed by adjusting the positions of respective parts of the substrates in conformity with the shapes of the respective parts of the irradiation target. A distance sensor that detects the distance between each light-emitting diode and the irradiation target may be installed, and based on the distance detected, the positions of the first longitudinal substrates 122 and the second longitudinal substrates 124 may be controlled. This arrangement can uniformly irradiate the respective parts of the irradiation target with the UV light at even intensity, and thus can prevent the damage to the skin due to the excessive irradiation with the UV light only on the specific part of the irradiation target. Further, the even good-looking tanning effect can be uniformly exhibited.

The controller 140 of the first embodiment further may include a lighting stopper 144 for stopping lighting on the irradiation target with the plurality of first light-emitting diodes 112 or the plurality of second light-emitting diodes 114, when the amount of irradiation on the irradiation target with the lights from the plurality of first light-emitting diodes 112 or the plurality of second light-emitting diodes 114 exceeds a preset value.

For example, an upper limit value of the total amount of the UVB light and/or the UVA light from the plurality of first light-emitting diodes 112 or second light-emitting diodes 114 to the irradiation target can be previously set based on the information about the relationship between the amount of irradiation with the UVB light or UVA light and the damage to the skin of the irradiation target. If the total amount of the UVB light and/or UVA light reaches the upper limit value, the lighting can be stopped.

In the first embodiment, a sensor 116 for measuring the total amounts of the UVB light and the UVA light applied to the irradiation target may be installed in the chamber 102. The sensor 116 transmits information regarding the amounts of irradiation with the UVB light and the UVA light applied to the irradiation target, to the controller 140. Based on the information transmitted from the sensor 116, when the amount of irradiation on the irradiation target with the lights from the first light-emitting diodes 112 or the second light-emitting diodes 114 exceeds the preset value, the lighting of the irradiation target by use of the plurality of first or second light-emitting diodes 112 or 114 is stopped.

Such a structure can prevent the damage to the skin of the irradiation target due to the excessive irradiation with the UV light based on the desire of the irradiation target that intends to gain the more tanning effect, or due to the excessive irradiation with the UV light caused by a human operation error.

In general, the tanning effect given by irradiation with the UVB light and the UVA light differs depending on the individual, race, gender, age, skin color, etc., of the irradiation target. Thus, the plurality of first light-emitting diodes 112 may include different types of first light-emitting diodes 112 with different peak wavelengths. For example, the appropriate type of first light-emitting diode 112 can be selected based on information about the individual of the irradiation target to irradiate the irradiation target with the UVB light having the appropriate peak wavelength. The same goes for the plurality of second light-emitting diodes 114.

Different parts of a UV light irradiation device 100 for suntan in the second embodiment from the first embodiment will be mainly described below. Other remaining parts of the UV light irradiation device 100 for suntan in the second embodiment may have the same structures as those in the first embodiment, unless otherwise specified.

In the second embodiment, the first light-emitting diodes 112 may include different types of the light-emitting diodes having different peak wavelengths, and the second light-emitting diodes 114 may include different types of the light-emitting diodes having different peak wavelengths.

The controller 140 may include a selector 143 for selecting one or more types of first light-emitting diodes 112 among the different types of first light-emitting diodes 112. The first light-emitting diodes 112 selected by the selector 143 can be lit up by the lighting control section 141. Likewise, the controller 140 may include the selector 143 for selecting one or more types of second light-emitting diodes 114 among the different types of second light-emitting diodes 114. The second light-emitting diodes 114 selected by the selector 143 can be lit up by the lighting control section 141. With such a form, the UV lights having appropriate peak wavelengths for the irradiation target are selected, and the irradiation target can be irradiated with the selected UV lights. Specifically, the most efficient tanning effect can be imparted to each individual as the irradiation target, based on the information regarding the relationship between the peak wavelengths of the UVA light and the UVB light and the amount of darkening of the skin in the irradiation target. Therefore, the adequate tanning effect can be obtained while suppressing the damage to the skin of the irradiation target due to irradiation with the UV light.

The plurality of first light-emitting diodes 112 may include the plurality of first light-emitting diodes 112 having respective peak wavelengths of three types of wavelength ranges. For example, the first light-emitting diodes may include a plurality of light-emitting diodes 1A having a peak wavelength in a range of 280 nm to 290 nm, a plurality of light-emitting diodes 1B having a peak wavelength in a range of 290 nm to 300 nm, and a plurality of light-emitting diodes 1C having a peak wavelength in a range of 300 nm to 310 nm. The plurality of first light-emitting diodes 112 may include a plurality of types of first light-emitting diodes 112, specifically, may include different types of first light-emitting diodes 112 having respective peak wavelengths in any different wavelength ranges set by dividing the wavelength range of 280 nm to 310 nm by 5 nm. Among these different types of first light-emitting diodes 112, the plurality of first light-emitting diodes 112 having an appropriate peak wavelength can be selected.

In this way, the plurality of different types of the first light-emitting diodes 112 can be provided to impart the more efficient tanning effect to the irradiation target, based on the information about the relationship between the peak wavelength of the UVB light and the amount of darkening of the skin in the irradiation target.

The plurality of second light-emitting diodes 114 may include a plurality of types of second light-emitting diodes 114, specifically, may include different types of second light-emitting diodes 114 having respective peak wavelengths in any different wavelength ranges set by dividing the wavelength range of 310 nm to 405 nm by 5 nm to 20 nm. Among these different types of second light-emitting diodes 114, the plurality of second light-emitting diodes 114 having an appropriate peak wavelength can be selected.

In this way, the plurality of different types of the second light-emitting diodes 114 can be provided to finely adjust the wavelength of the UVA light applied to the irradiation target, thereby imparting the more efficient tanning effect to the irradiation target, based on the information about the relationship between the peak wavelength of the UVA light and the amount of darkening of the skin in the irradiation target.

In the specification, the UV in a short wavelength range of less than 280 nm is classified as the ultraviolet C wave (UVC). In general, the UVC light is known to inflict serious damage to the skin or eye of the irradiation target as compared to the UV light having a wavelength range of 280 nm or more. FIG.

Figure 6:
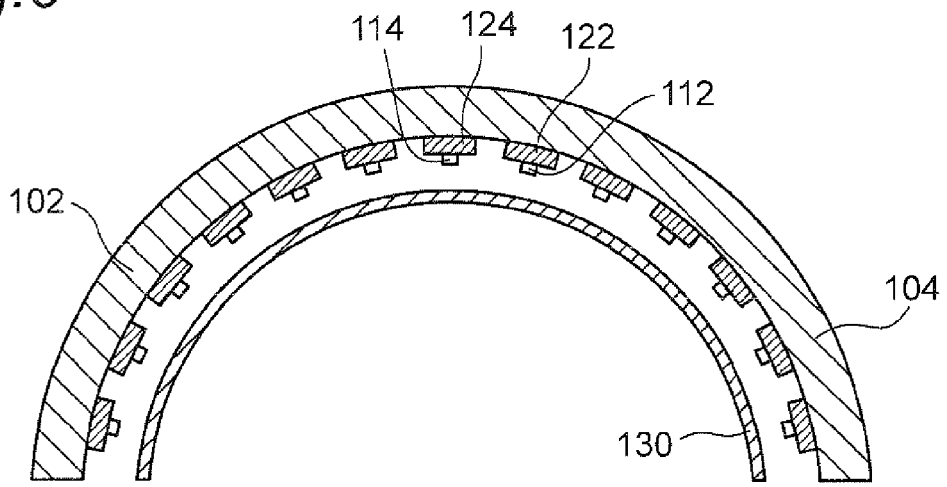
FIG. 6 is a cross-sectional view taken along the line X-X of FIG. 3 according to a second embodiment.

6 is a cross-sectional view taken along the line X-X of FIG. 3 according to a second embodiment. In the second embodiment, the UV light irradiation portion 101 in the UV light irradiation device 100 for suntan may include a filter 130 for excluding the UV light having a wavelength of less than 280 nm. As illustrated in FIG. 6, the filter 130 is disposed between the irradiation target, and the plurality of first light-emitting diodes 112 and the plurality of second light-emitting diodes 114. In this way, the irradiation target can be effectively tanned while suppressing the damage to the skin.

DESCRIPTION OF REFERENCE NUMERALS

100: UV light irradiation device
101: UV light irradiation portion
102: Chamber
104: First cover
106: Second cover
108: Coupling element
110: A plurality of light-emitting diodes
112: First light-emitting diode
114: Second light-emitting diode
116: Sensor
120: A plurality of substrates
122: First longitudinal substrate
124: Second longitudinal substrate
130: Filter
140: Controller
141: Lighting control section
142: Light emission intensity control section
143: Selector
144: Lighting stopper

What is claimed is:

1. A ultraviolet light irradiation device, comprising:
a chamber having a space for accommodating therein an irradiation target;
a plurality of light-emitting diodes provided at an inner surface of the chamber; and
a controller configured to control lighting of the plurality of light-emitting diodes,
wherein
the plurality of light-emitting diodes include
a plurality of first light-emitting diodes, each having a peak wavelength in a range of 280 nm to 310 nm, and
a plurality of second light-emitting diodes, each having a peak wavelength in a range of 310 nm to 405 nm, and
wherein the controller includes a lighting control section configured to light up the first light-emitting diodes before lighting up the second light-emitting diodes.

2. The ultraviolet light irradiation device according to claim 1, wherein the lighting control section is configured to adjust the lighting time of the plurality of the first light-emitting diodes and the lighting time of the plurality of the second light-emitting diodes.

3. The ultraviolet light irradiation device according to claim 1, wherein the lighting control section is configured to alternately light up the plurality of the first light-emitting diodes and the plurality of the second light-emitting diodes.

4. The ultraviolet light irradiation device according to claim 1, wherein the lighting control section is configured to light up the plurality of the second light-emitting diodes before stopping lighting the plurality of the first light-emitting diodes.

5. The ultraviolet light irradiation device according to claim 4,
wherein the plurality of first light-emitting diodes comprise different types of first light-emitting diodes with different peak wavelengths, the controller comprises a selector configured to select one or more types of first light-emitting diodes among the different types of first light-emitting diodes, and the first light-emitting diodes selected by the selector are lit up by the lighting control section,
wherein the different types of the plurality of first light-emitting diodes comprise a plurality of light-emitting diodes 1A having a peak wavelength in a range of 280 nm to 290 nm, a plurality of light-emitting diodes 1B having a peak wavelength in a range of 290 nm to 300 nm, and a plurality of light-emitting diodes 1C having a peak wavelength in a range of 300 nm to 310 nm.

6. The ultraviolet light irradiation device according to claim 4, further comprising a filter for excluding the UV light having a wavelength of less than 280 nm disposed between the irradiation target, and the plurality of first light-emitting diodes and the plurality of second light-emitting diodes.

7. The ultraviolet light irradiation device according to claim 6, wherein the controller comprises a lighting stopper configured to stop lighting on the irradiation target with the plurality of first light-emitting diodes or the plurality of second light-emitting diodes when the amount of irradiation on the irradiation target with the lights from the plurality of first light-emitting diodes or the plurality of second light-emitting diodes exceeds a preset value.

8. The ultraviolet light irradiation device according to claim 7, further comprising substrates provided along the inner surface of the chamber,
wherein the plurality of light-emitting diodes is provided on each of the substrates,
wherein the substrates comprise first substrate and second substrate, wherein the plurality of first light-emitting diodes is provided on the first substrate and the plurality of second light-emitting diodes is provided on the second substrate,
wherein the first substrates comprise a plurality of first longitudinal substrates each having long side and short side, and the second substrates comprise a plurality of second longitudinal substrates each having long side and short side,
wherein the first and second longitudinal substrates are alternately arranged.

9. The ultraviolet light irradiation device according to claim 4, wherein the controller comprises a lighting stopper configured to stop lighting on the irradiation target with the plurality of first light-emitting diodes or the plurality of second light-emitting diodes when the amount of irradiation on the irradiation target with the lights from the plurality of first light-emitting diodes or the plurality of second light-emitting diodes exceeds a preset value.

10. The ultraviolet light irradiation device according to claim 4, further comprising substrates provided along the inner surface of the chamber,
wherein the plurality of light-emitting diodes is provided on each of the substrates,
wherein the substrates comprise first substrate and second substrate, wherein the plurality of first light-emitting diodes is provided on the first substrate and the plurality of second light-emitting diodes is provided on the second substrate,
wherein the first substrates comprise a plurality of first longitudinal substrates each having long side and short side, and the second substrates comprise a plurality of second longitudinal substrates each having long side and short side, and wherein the first and second longitudinal substrates are alternately arranged.

11. The ultraviolet light irradiation device according to claim 1, wherein the controller comprises a light emission intensity control section configured to individually control the light emission intensities of lights from the plurality of first light-emitting diodes and the light emission intensities of lights from the plurality of second light-emitting diodes.

12. The ultraviolet light irradiation device according to claim 1, wherein the plurality of first light-emitting diodes comprise different types of first light-emitting diodes with different peak wavelengths, the controller comprises a selector configured to select one or more types of first light-emitting diodes among the different types of first light-emitting diodes, and the first light-emitting diodes selected by the selector are lit up by the lighting control section.

13. The ultraviolet light irradiation device according to claim 12, wherein the different types of the plurality of first light-emitting diodes comprise a plurality of light-emitting diodes 1A having a peak wavelength in a range of 280 nm to 290 nm, a plurality of light-emitting diodes 1B having a peak wavelength in a range of 290 nm to 300 nm, and a plurality of light-emitting diodes 1C having a peak wavelength in a range of 300 nm to 310 nm.

14. The ultraviolet light irradiation device according to claim 1, wherein the plurality of second light-emitting diodes comprises different types of second light-emitting diodes with different peak wavelengths, the controller comprises a selector for selecting one or more types of second light-emitting diodes among the different types of second light-emitting diodes, and the second light-emitting diodes selected by the selector are lit up by the lighting control section.

15. The ultraviolet light irradiation device according to claim 1, further comprising a filter which is configured to exclude the UV light having a wavelength of less than 280 nm disposed between the irradiation target, and the plurality of first light-emitting diodes and the plurality of second light-emitting diodes.

16. The ultraviolet light irradiation device according to claim 1, wherein the controller comprises a lighting stopper configured to stop lighting on the irradiation target with the plurality of first light-emitting diodes or the plurality of second light-emitting diodes when the amount of irradiation on the irradiation target with the lights from the plurality of first light-emitting diodes or the plurality of second light-emitting diodes exceeds a preset value.

17. The ultraviolet light irradiation device according to claim 1, further comprising substrates provided along the inner surface of the chamber, wherein the plurality of light-emitting diodes is provided on each of the substrates.

18. The ultraviolet light irradiation device according to claim 17, wherein the substrates comprise first substrate and second substrate, wherein the plurality of first light-emitting diodes is provided on the first substrate and the plurality of second light-emitting diodes is provided on the second substrate.

19. The ultraviolet light irradiation device according to claim 18, wherein the first substrates comprise a plurality of first longitudinal substrates each having long side and short side, and the second substrates comprise a plurality of second longitudinal substrates each having long side and short side.

20. The ultraviolet light irradiation device according to claim 19, wherein the first and second longitudinal substrates are alternately arranged.

* * * * *